(12) United States Patent
Fuhrmann et al.

(10) Patent No.: US 7,596,206 B2
(45) Date of Patent: Sep. 29, 2009

(54) RADIOGRAPHY DEVICE FOR RECORDING DYNAMIC PROCESSES AND ASSOCIATED RECORDING METHOD

(75) Inventors: Michael Fuhrmann, Herzogenaurach (DE); Mathias Hörnig, Erlangen (DE); Michael Maschke, Lonnerstadt (DE); Doris Pommi, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/810,973

(22) Filed: Jun. 7, 2007

(65) Prior Publication Data
US 2007/0286334 A1    Dec. 13, 2007

(30) Foreign Application Priority Data
Jun. 8, 2006    (DE) ...................... 10 2006 026 722

(51) Int. Cl.
*G01N 23/04* (2006.01)
(52) U.S. Cl. .......................................... 378/62; 378/116
(58) Field of Classification Search .................. 378/62, 378/64, 65, 68, 69, 98.8, 98.9, 114–116; 250/370.09
See application file for complete search history.

(56) References Cited

U.S. PATENT DOCUMENTS

| | | | | |
|---|---|---|---|---|
| 3,932,759 A * | 1/1976 | Brundin | ........................ | 378/98 |
| 6,236,712 B1 * | 5/2001 | Tomasetti et al. | ........... | 378/114 |
| 6,647,093 B2 * | 11/2003 | Schmitz et al. | .............. | 378/108 |
| 6,659,641 B2 * | 12/2003 | Schwieker | .................. | 378/196 |
| 6,807,250 B2 * | 10/2004 | Wang et al. | ................... | 378/63 |
| 6,851,851 B2 * | 2/2005 | Smith et al. | ................. | 378/189 |

OTHER PUBLICATIONS

Dr. Ralph Hausmann, "Bessere Bilder und geringere Strahlenbelastung", Thieme Fachzeitschriften, Mar. 2004, pp. 1-2, Frankfurt, Retrieved from Internet, Mar. 3, 2007, http://www.thieme.de/fz/roefo/03_04/brenn_05.html.

* cited by examiner

*Primary Examiner*—Jurie Yun

(57) ABSTRACT

There is described a radiography device for recording dynamic processes and an associated recording method. The radiography arrangement is used to examine patients using an x-ray source, a digital flat detector with a single shot recording function and an operating console for controlling and recording purposes, with the flat detector also being able to display an image sequence at a rate of up to 5 Hertz, which allows the positioning of the region to be examined or the monitoring of pseudo-interventional interventions.

15 Claims, 6 Drawing Sheets

FIG 6  Basic sequence
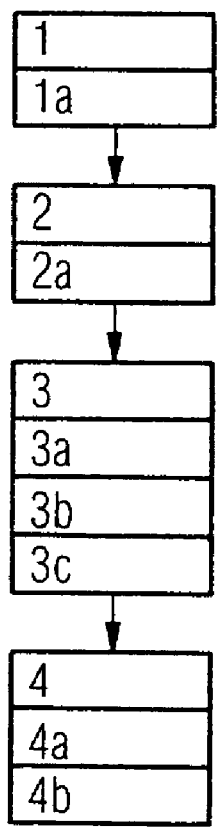
FIG 7  Alternative sequence 1
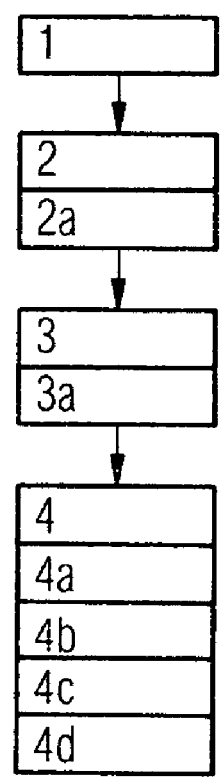
FIG 8  Alternative sequence 2
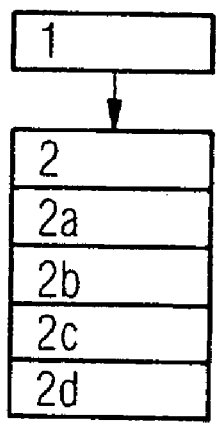

RADIOGRAPHY DEVICE FOR RECORDING DYNAMIC PROCESSES AND ASSOCIATED RECORDING METHOD

CROSS REFERENCE TO RELATED APPLICATIONS

This application claims priority of German application No. 10 2006 026 722.2 DE filed Jun. 8, 2006, which is incorporated by reference herein in its entirety.

FIELD OF INVENTION

The present invention relates to a radiography arrangement for examining patients, with an x-ray source, a flat detector with a single shot recording function and an operating console to control the recording process. The present invention also relates to a method for examining patients using a radiography arrangement with an x-ray source, a digital flat detector and a single shot recording function.

BACKGROUND OF INVENTION

X-ray systems today generally have to be assigned in a dedicated manner to one clinical field of application. A distinction is therefore made between C-arm angiography systems, fluoroscopy systems and radiography systems. The first two system groups mentioned can deal with both dynamic applications and single shot recordings, while to date only single shot recordings are possible with radiography systems. Radiography systems are used when single shots have to be recorded with very high resolution, for example to show fine cracks. With fluoroscopy it is possible to record up to 30 images/s but only ⅓ the resolution of images from radiography systems can be achieved in the process. Combination systems are currently used, which combine the fluoroscopy functionality and the single shot recording function as analog facilities in one device. Fluoroscopy here uses a camera with a light amplifier, while single shot recording uses a cassette. If digital flat detectors are used as the detectors in the combination systems, only image sizes of 20 cm×20 cm are possible due to the large volumes of data. When examining major organs (such as lung and pelvis) a detector size of minimum 35 cm×35 cm and preferably 42 cm×42 cm is used. If a digital flat detector of this size is used, the volumes of data are too large to image dynamic processes. An image from a flat detector with 9 megapixels and a size of 42 cm×42 cm supplies a volume of data of approx. 20 MB per image. The problem is that radiography systems cannot record time-limited dynamic applications in addition to single shot recordings, mainly due to the available detectors, such as analog film, analog imaging plates or digital flat detectors, which do not support this functionality.

SUMMARY OF INVENTION

Based on the discussed disadvantages and problems above, an object is to develop a radiography system with a flat detector in such a manner that it is possible to record and display time-limited dynamic applications as well as single shot recordings. It is important here to keep the radiation load on the patient as low as possible. The present object is achieved by a device with the features of a independent claim and by a method with the features of a further independent claim. The present invention is advantageous for a number of reasons. The function that allows an image sequence to be recorded at a rate of up to 5 Hertz means that positioning can be achieved, which allows single shot recordings or the monitoring of an intervention. Positioning allows incorrect images to be avoided during single shot recording. It is particularly advantageous here that the radiation load for the patient is very low when recording a dynamic application. Also a set of parameters is available for every organ to be examined for recording purposes, so that an optimum image can be produced for every organ. The present invention also describes a method for positioning the examination area before recording single shots or for monitoring interventions.

BRIEF DESCRIPTION OF THE DRAWINGS

The invention is described in more detail below based on the description of preferred exemplary embodiments with reference to the drawings, in which:

FIG. 6 shows a flow diagram just for positioning patients FIG. 7 shows a flow diagram for positioning patients followed by single shot recording FIG. 8 shows a flow diagram for positioning patients and for recording single shots in any sequence with uses inside and/or outside the examination room

DETAILED DESCRIPTION OF INVENTION

Figure 1:
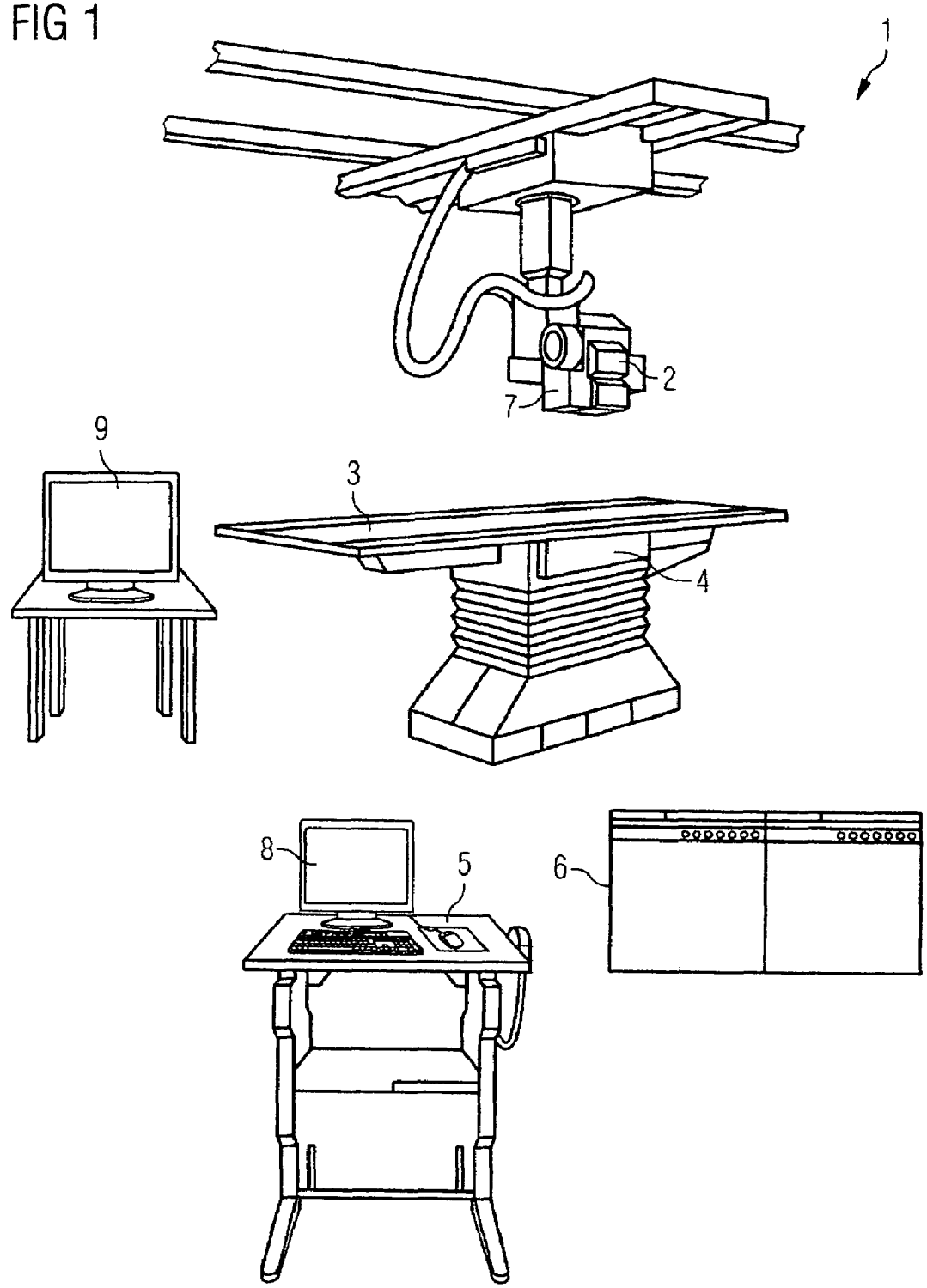
FIG. 1 shows a schematic diagram of a radiography arrangement with emitter on the ceiling and detector integrated in the table

FIG. 1 shows a first exemplary embodiment of the present invention. It is a radiography arrangement (1) with flat detector technology, the arrangement having a table device with emitter (2) on the ceiling, a table (3) with integrated detector (4) for prone applications, an operating console (5) (computer) and a generator with system cabinet (6). The radiography arrangement (1) is used to examine patients, using an x-ray source (2), a digital flat detector (4) with a single shot recording function and an operating console (5) for controlling and recording purposes, with the flat detector (4) also being equipped with the function of recording an image sequence at a recording rate of 1 to 5 Hertz and preferably 3 Hertz. This allows positioning of the region to be examined or monitoring during pseudo-interventional interventions. During recordings for positioning in respect of an organ and during pseudo-interventional interventions, such as positioning a catheter or needle for tissue samples in relation to the same organ, the same radiation dose is used, while for recording single shots of said organ a radiation dose up to a factor 10 higher is used. The method can be compared with a digital video film, which runs until the required organ can be displayed as precisely as possible. The digital flat detector (4) has an electronic read-out system, which requires minimum ⅕ s for a cycle consisting of clearing, recording and reading out a measurement pulse, so that an image rate of up to 5 Hertz is possible for recording dynamic applications. Positioning is effected by means of a controller, which is based on an organ program function, having a set of parameters, which is a function of the organ to be examined and includes parameters for generation of the high voltage to produce the x-ray radiation (generator parameters), for image processing, for overlaying (limiting the x-ray beam) and for the image rate, in order to produce an optimum image for each organ. The x-ray beam is limited to the size of the examination area by means of overlay frames (7) with lead strips in the beam path. Overlaying means that only the area to be examined is irradiated. During a recording the x-ray light that has passed through the medium to be examined strikes a scintillator, where it is converted to light, which strikes the detector. A monitor (8) is provided at the operating console (5) to display the positioning process at maximum 5 images/s in real time and, if required, the following single shot. A separate monitor (9) is also provided, which is installed in proximity to the patient and which displays the last image of the positioning process in each instance (LIH: Last image hold). A digital flat detector (4) with a size of at least 35 cm×35 cm and preferably 42 cm×42 cm is used, to image large examination areas such as pelvis or lung. A particular benefit of the invention is that radiography systems with the capability of producing dynamic images are much cheaper and have a higher image quality than the combination systems mentioned in the prior art. Only for a small percentage of applications is the image rate of the radiography system of maximum 5 Hertz insufficient to image dynamic processes precisely. In these instances it is then necessary to use conventional fluoroscopy systems, which permit image rates of up to 30 images per second.

Figure 2:
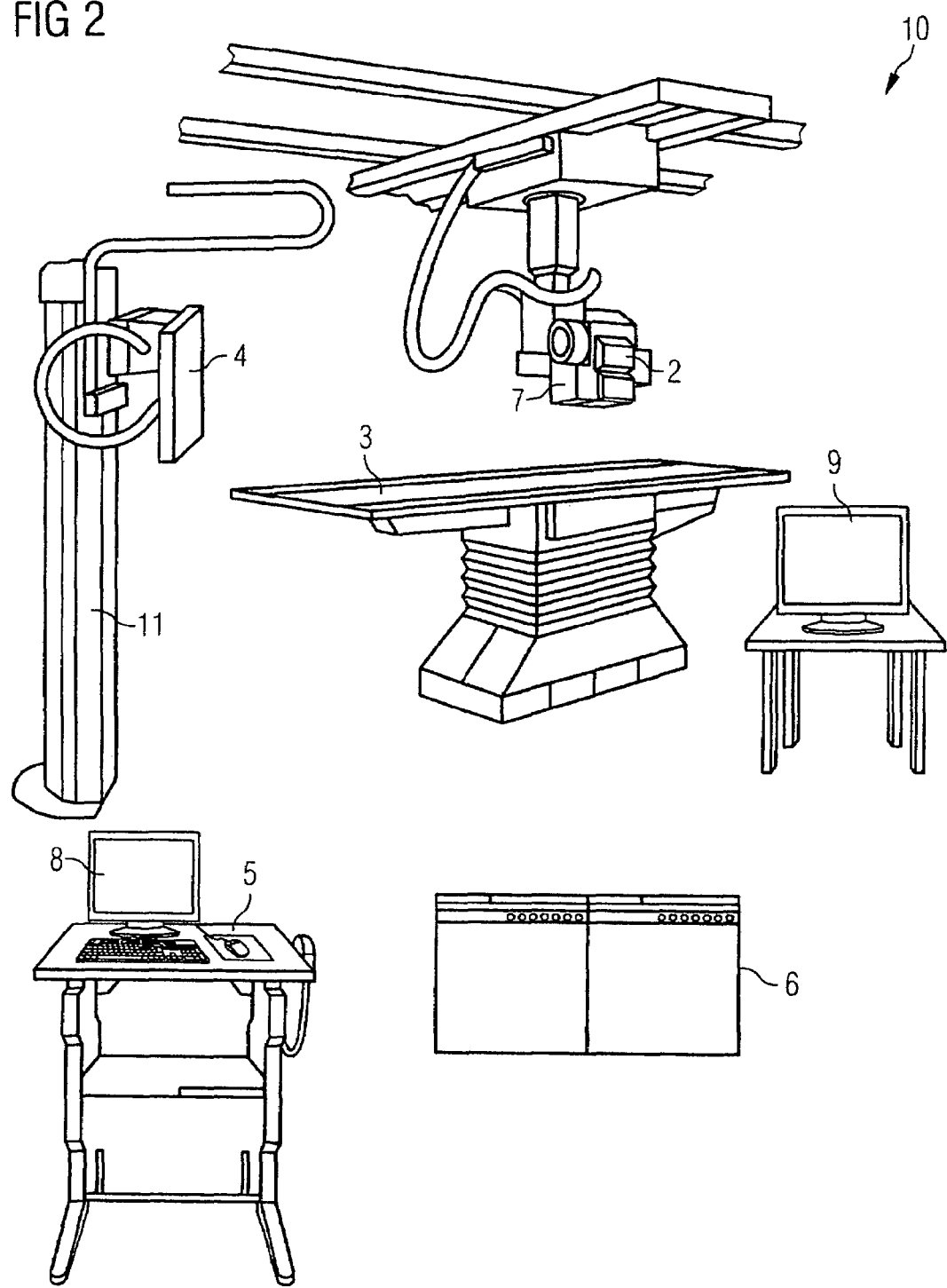
FIG. 2 shows a schematic diagram of a radiography arrangement with emitter on the ceiling and additional (to the table) wall device with detector

FIG. 2 shows a second exemplary embodiment of the present invention. The radiography arrangement (10) is equipped with a flat detector (4), the arrangement having a table device with emitter (2) on the ceiling, as well as a wall device (11) with detector (4) for standing recordings, an operating console (5) (computer) and a generator with system cabinet (6). FIG. 2 differs from FIG. 1 only in the additional wall device with flat detector (4). Otherwise all the characteristics and functions correspond to those shown in FIG. 1.

Figure 3:
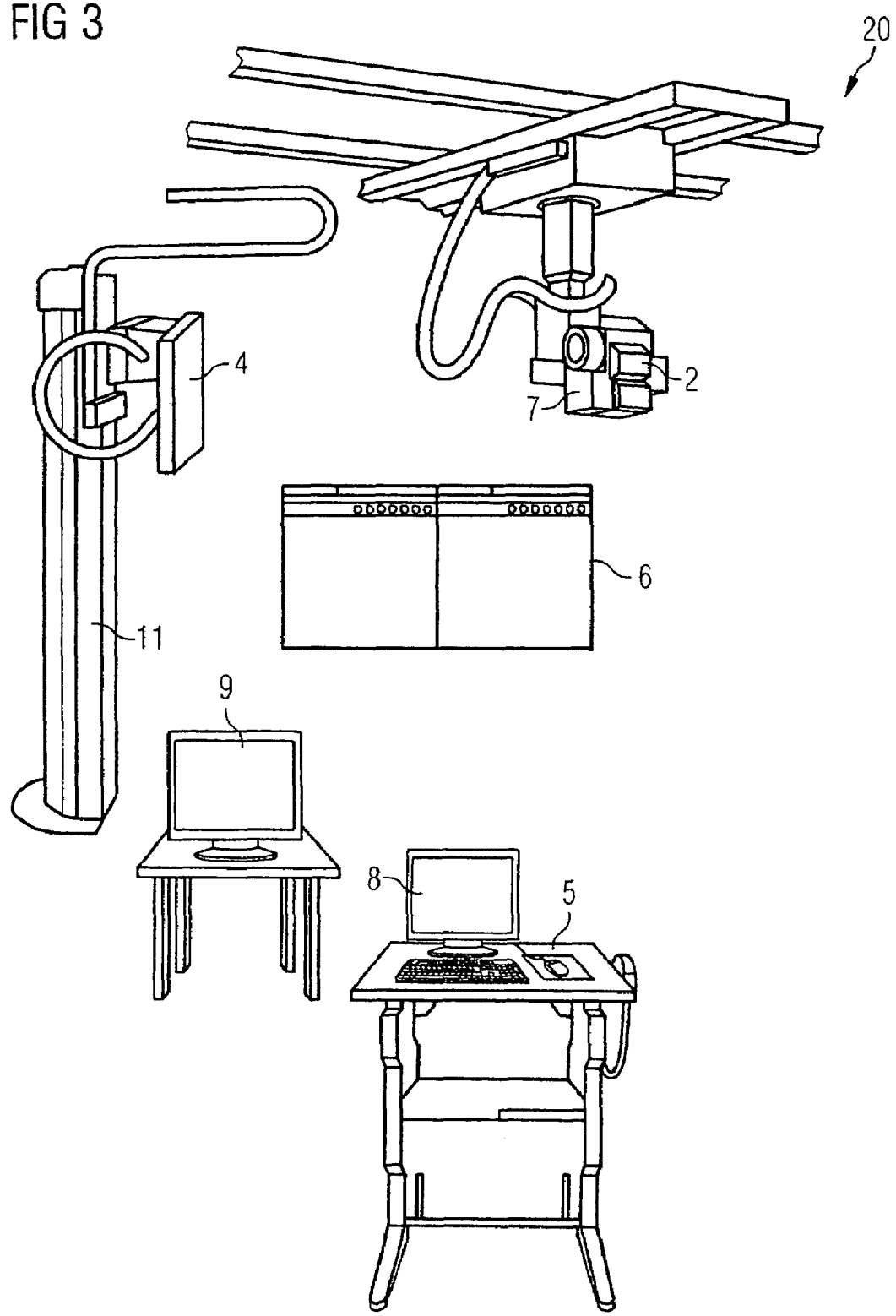
FIG. 3 shows a schematic diagram of a radiography arrangement with emitter on the ceiling and wall device with detector

FIG. 3 shows a third exemplary embodiment of the present invention. The radiography arrangement (20) is equipped with a flat detector (4), the arrangement having a wall device (11) with emitter (2) on the ceiling, a detector (4) in the wall device (11) for standing recordings, an operating console (5) (computer) and a generator with system cabinet (6). Compared with FIG. 1, in FIG. 3 a wall device with flat detector is used instead of the table. Otherwise all the characteristics and functions correspond to those shown in FIG. 1.

Figure 4:
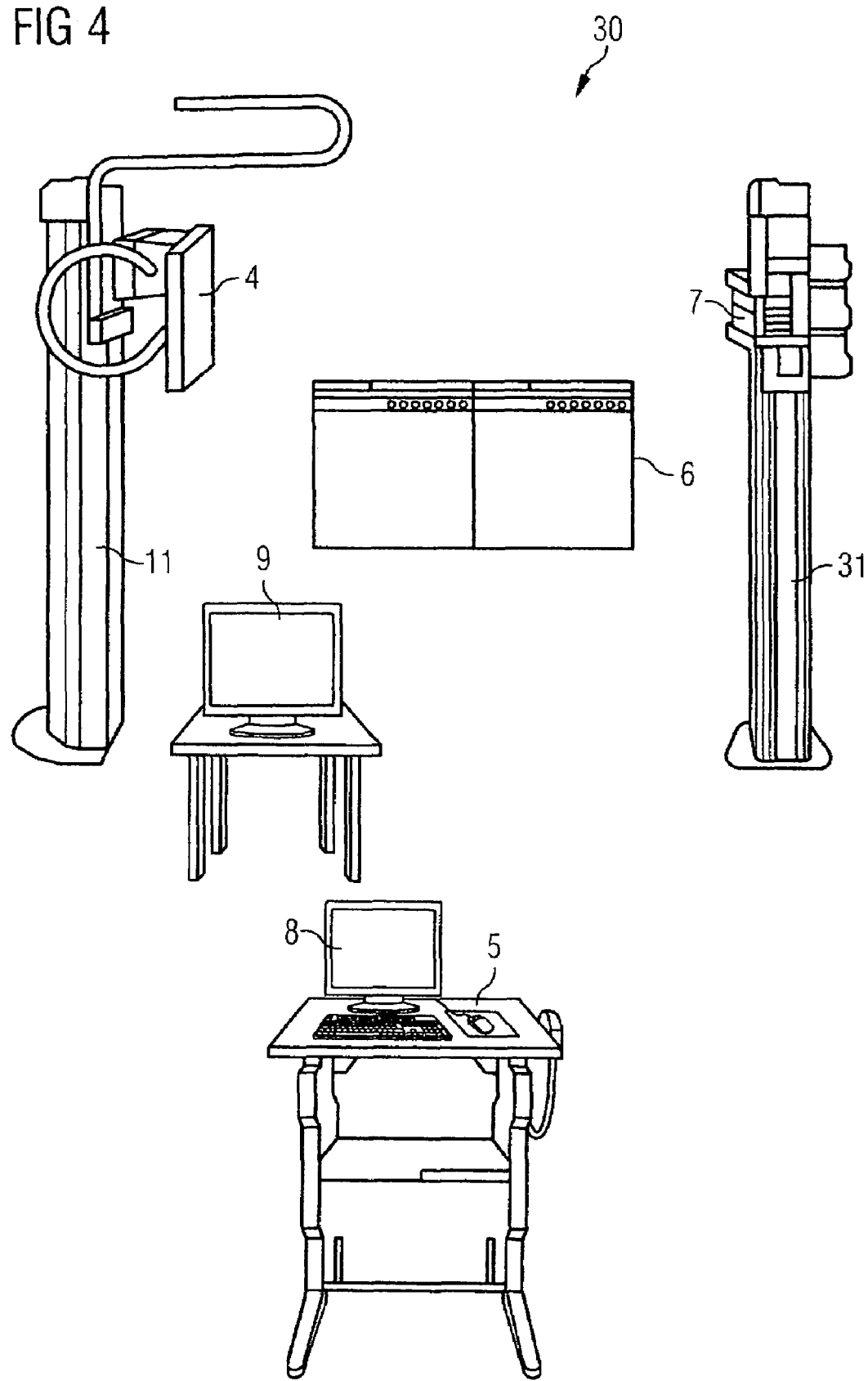
FIG. 4 shows a schematic diagram of a radiography arrangement with emitter on the floor and wall device with detector

FIG. 4 shows a fourth exemplary embodiment of the present invention. The radiography arrangement (30) is equipped with a flat detector (4), the arrangement having a wall device (11) with emitter (31) on the floor, a detector (4) in the wall device (11) for exclusively standing recordings, an operating console (5) (computer) and a generator with system cabinet (6). Compared with FIG. 1, in FIG. 4 a wall device is used instead of the table and an emitter on the floor instead of the emitter on the ceiling. Otherwise all the characteristics and functions correspond to those shown in FIG. 1.

Figure 5:
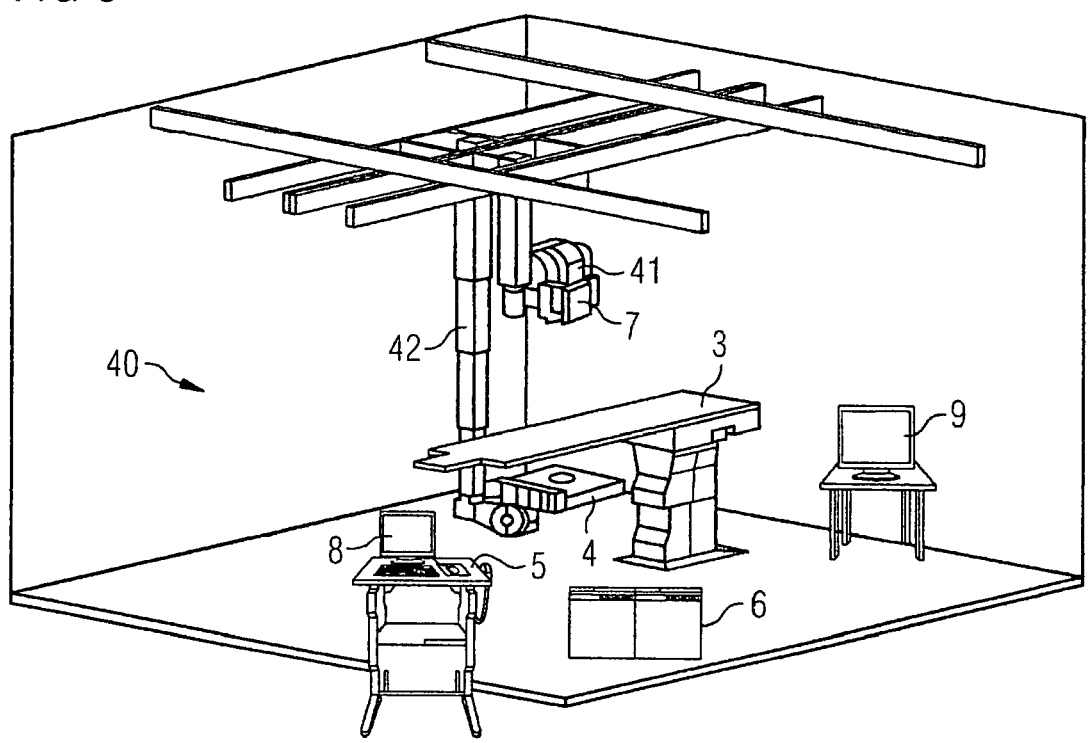
FIG. 5 shows a schematic diagram of a radiography arrangement with freely positionable emitter and detector

FIG. 5 shows a fifth exemplary embodiment of the present invention. The radiography arrangement (40) is equipped with a flat detector (4), the arrangement being a universal device, which, suspended from the ceiling, has an emitter (41) that can be positioned freely around a table and a detector arm (42) attached to the ceiling with a detector (4), an operating console (5) (computer) and a generator with system cabinet (6). The possible positions can be assumed automatically according to the organ program function. In contrast to FIG. 1, FIG. 5 shows an emitter and detector that can be moved freely around the table, both being attached to the ceiling. Otherwise all the characteristics and functions correspond to those shown in FIG. 1.

A method is also developed in the invention to examine patients using a radiography arrangement (1) with an x-ray source (2) and a digital flat detector (4), with single shots and/or a sequence of recordings being recorded to position the area to be examined or to monitor interventions. The recording rate is between 1 and 5 Hertz and preferably 3 Hertz. To protect the patient the recording period during positioning or during pseudo-interventional interventions can be limited to 3 seconds. In contrast to recordings using fluoroscopy systems, where the patient is generally prone and the table is moved, during recordings with radiography systems the patient can be in any position, for instance prone, standing or sitting. During radiography recordings the x-ray source is generally moved. To avoid incorrect images, the region to be examined is positioned immediately before the single shot recording, with a series of images being recording during positioning, the respective intensity of which is up to a factor 10 less than the intensity during a single shot recording. The changeover period between positioning and single shot recording is around 700 ms, thereby preventing movement effects. The changeover between positioning and single shot recording is achieved not manually but by means of a foot switch or by voice instructions. Two operating positions can be used simultaneously for a recording (series), for instance with one user directly by the patient in the examination room and/or a further user at the operating console outside the examination room.

The rough sequence in principle of a recording using a radiography system and flat detector is set out below. First the organ parameters are selected, then the preliminary settings are established, then the radiation is triggered for the positioning process, then the position and overlay are adjusted, then positioning is terminated and finally the single shot recording is taken.

FIGS. 6, 7, 8 show individual steps for three different recording methods in detail.

FIG. 6 shows a first flow diagram with individual steps of the method, according to which the present invention operates during positioning or during the monitoring of pseudo-interventional interventions. In method step 1 the user registers the patient and selects the organ program. In step 1a the system supplies the correct parameters. In step 2 the user positions the patient and system roughly. In step 2a the system is ready. In step 3 the radiology technician and/or radiologist or another doctor carries out an intervention on the patient. In step 3a the system allows up to 5 images per second, preferably 3 images per second, with a total of 10-100 images, or at least 10 images and preferably 30 images. In step 3b the system displays images close to the patient with an appropriate image quality (LIH: Last Image Hold). In step 3c the system makes the entire functionality available at the patient's side. In step 4 the user only uses series of recordings with a low x-ray dose, without changing the parameters. In step 4a the system makes all the images available in a patient folder. In step 4b the system allows the images to be printed out, sent and stored in any sequence.

FIG. 7 shows a second flow diagram with individual steps of the method, according to which the present invention operates during positioning followed by single shot recording. Step 1 of the second flow diagram combines all the steps 1 to 3c from FIG. 6 of the first flow diagram. In step 2 the user takes series of recordings with a low x-ray dose (positioning) and single shot recordings in different directions and at different times. In step 2a the system switches between recordings with a low x-ray dose (positioning) and single shot recording in less than 700 ms. In step 3 the user is able to change the parameters quickly and simply from within the examination room. In step 3a the system is able to change all the parameters. In step 4 the user can switch quickly and simply between a series of recordings with a low x-ray dose (positioning) and a single shot recording, without having to use their hands. In step 4a the system allows simple handling. In step 4b the system allows switching to and fro between a series of recordings with a low radiation dose and a single shot recording, controlled by a foot switch or by voice recognition. In step 4c the system makes all the recording series functionalities with a low x-ray dose (positioning) available, such as LIH (Last Image Hold) or care profile (pulsed fluoroscopy with a low level of x-ray intensity). In step 4d the system allows the images to be printed out, sent and stored in any sequence.

FIG. 8 shows a third flow diagram with individual steps of the method, according to which the present invention operates, when users are operating simultaneously inside and outside the examination room. Step 1 of the third flow diagram combines all the steps 1 to 3c from FIG. 6 of the first flow diagram. In step 2 the user is inside the examination room to set parameters and at the same time the radiology technician is outside the examination room, to set parameters at the operating console there. In step 2a the system supplies parameters inside and outside the examination room. In step 2b the system provides the option of fast changes. In step 2c the sequence of the recording series with a low x-ray dose and single shot recording is optional. In step 2d the system allows the images to be printed out, sent and stored in any sequence.

The invention claimed is:

1. A radiography arrangement to examine a patient, comprising:
    a x-ray source;
    a digital flat detector with a single shot recording function and a further function to record an image sequence at a recording rate of 1 to 5 Hertz to position a region of the patient; and
    an operating console including a controller for controlling, positioning and recording, the console configured to provide for recording an image sequence of an organ at a first radiation dose followed by providing for recording of a single shot of the organ at a second radiation dose up to a factor of ten higher than the first dose, wherein the positioning is based on an organ program function, having a set of parameters, wherein the set of parameters is dependent on the organ to be examined, and wherein the organ program function has parameters for generating high voltage to produce an x-ray radiation, for image processing, for overlaying to limit an x-ray beam and for a image rate in order to produce an optimum image for an organ.

2. The radiography arrangement as claimed in claim 1, wherein the digital flat detector has an electronic read-out system having a cycle of minimum ⅕ second to delete, to record and to read a measurement pulse, to allow an image rate of up to 5Hertz for recording dynamic applications.

3. The radiography arrangement as claimed in claim 1, wherein the x-ray beam is limited to the size of a examination area based upon overlay frames with lead strips in a beam path, wherein the digital flat detector has a size of at least 35 cm×35 cm.

4. The radiography arrangement as claimed in claim 1, wherein a monitor at the operating console displays a positioning at maximum 5 images per second in real time followed by a single shot.

5. The radiography arrangement as claimed in claim 4, wherein a separate monitor is installed in proximity to the patient to display the last image of a positioning process.

6. The radiography arrangement as claimed in claim 1, wherein the radiography arrangement has a table device, the x-ray source on the ceiling, a table with the digital flat detector being integrated for prone applications, an operating console and a generator with a system cabinet.

7. The radiography arrangement as claimed in claim 6, wherein a basic position is adjusted manually.

8. The radiography arrangement as claimed in claim 1, wherein the radiography arrangement has a table device with the x-ray source on a ceiling, a wall device with the digital flat detector for standing recordings, an operating console, and a generator with a system cabinet.

9. The radiography arrangement as claimed in claim 1, wherein the radiography arrangement has a wall device with the digital flat detector, the x-ray source on a ceiling, an operating console, a generator, and a system cabinet.

10. The radiography arrangement as claimed in claim 1, wherein the radiography arrangement has a wall device with the digital flat detector, the x-ray source on a floor, an operating console, a generator, and a system cabinet, wherein the radiography arrangement is used only for standing recordings of a patient.

11. The radiography arrangement as claimed in claim 1, wherein the radiography arrangement is suspended from a ceiling, has the x-ray source to be positioned freely around a table and the digital flat detector arm attached to the ceiling with the digital flat detector for prone recordings, an operating console, a generator, and a system cabinet, and wherein a position is assumed automatically based upon the organ program function.

12. A method for examining patients based upon a radiography arrangement having a single shot recording function, comprising:
    providing an x-ray source;
    providing a digital flat detector;
    positioning the patient for recording an area to be examined by first recording a sequence of images at a recording rate of 1 to 5 Hertz, thereby avoiding recording an incorrect image; and
    then providing a single shot recording, wherein the positioning further includes adjusting a set of parameters for an organ program function, wherein the parameters are dependent on an organ to be examined, and wherein the parameters relate to generating high voltage to produce x-ray radiation, image processing, overlaying to limit an x-ray beam and selecting an image rate in order to produce an optimum image for an organ.

13. The method as claimed in claim 12, wherein the recording period is limited to 3 seconds.

14. The method as claimed in claim 12, wherein for the recording of a sequence of images a respective beam intensity is up to a factor 10 lower than the beam intensity during the single shot recording, wherein a changeover period between the sequence of images and the single shot recording is essentially 700 ms.

15. The method as claimed in claim 12, further including switching between the recording of a sequence of images and the single shot recording without using hands, but by using a foot switch or voice instructions.

* * * * *